(12) United States Patent
Matsui et al.

(10) Patent No.: US 10,188,491 B2
(45) Date of Patent: Jan. 29, 2019

(54) DENTAL RESTORATION PRODUCING SYSTEM FOR PRODUCING DENTAL RESTORATION FROM DENTAL MILL BLANK WITH THROUGH-HOLE, OPERATION SYSTEM OF THE SYSTEM, PROGRAM FOR THE SYSTEM, AND DENTAL MILL BLANK FOR USE IN THE SYSTEM

(71) Applicant: SHOFU INC., Kyoto (JP)

(72) Inventors: Norihiro Matsui, Kyoto (JP); Yusei Kadobayashi, Kyoto (JP)

(73) Assignee: SHOFU INC., Kyoto (JP)

( * ) Notice: Subject to any disclaimer, the term of this patent is extended or adjusted under 35 U.S.C. 154(b) by 277 days.

(21) Appl. No.: 15/249,673

(22) Filed: Aug. 29, 2016

(65) Prior Publication Data
US 2017/0056137 A1    Mar. 2, 2017

(30) Foreign Application Priority Data

Aug. 31, 2015 (JP) .................................. 2015-169914
May 20, 2016 (JP) .................................. 2016-100998

(51) Int. Cl.
*A61C 13/00* (2006.01)

(52) U.S. Cl.
CPC ...... *A61C 13/0004* (2013.01); *A61C 13/0006* (2013.01); *A61C 13/0022* (2013.01)

(58) Field of Classification Search
USPC .................................................... 700/95–212
See application file for complete search history.

(56) References Cited

U.S. PATENT DOCUMENTS

| 4,530,046 A | * | 7/1985 | Munekata | ........ | G05B 19/40935 |
|---|---|---|---|---|---|
| | | | | | 318/568.1 |
| 2002/0076530 A1 | * | 6/2002 | MacDougald | ..... | A61C 13/0003 |
| | | | | | 428/195.1 |

* cited by examiner

*Primary Examiner* — Kenneth M Lo
*Assistant Examiner* — Istiaque Ahmed
(74) *Attorney, Agent, or Firm* — Wenderoth, Lind & Ponack, L.L.P.

(57) ABSTRACT

A dental restoration producing system of producing a dental restoration from a dental mill blank with one or more through-holes according to one embodiment, when the dental restoration includes no through-hole of the dental restoration, the superposed data generating section generates a superposed data in which at least one through-hole of the dental mill blank is not superposed with the dental restoration, when the dental restoration includes a through-hole of the dental restoration, the superposed data generating section generates a superposed data in which at least one through-hole of the dental mill blank is not superposed with the dental restoration and the through-hole of the dental restoration, or a superposed data in which at least one through-hole of the dental mill blank is included in the through-hole of the dental restoration which is larger than the at least one through-hole of the dental mill blank.

5 Claims, 7 Drawing Sheets

DENTAL RESTORATION PRODUCING SYSTEM FOR PRODUCING DENTAL RESTORATION FROM DENTAL MILL BLANK WITH THROUGH-HOLE, OPERATION SYSTEM OF THE SYSTEM, PROGRAM FOR THE SYSTEM, AND DENTAL MILL BLANK FOR USE IN THE SYSTEM

BACKGROUND OF THE INVENTION

Field of the Invention

The present disclosure relates a dental restoration producing system for producing a dental restoration from a dental mill blank with a through-hole, an operation method of the system, a program for the system, and a dental mill blank for use in the system.

Description of the Related Art

In the dental field, a method of preparing of a dental restoration by cutting of a block or a disk which are dental mill blanks using CAD/CAM technique is known.

For example, PCT International Publication No. WO 2014/013824 (WO2014/013824A1) and Japanese Unexamined Patent Application Publication (Translation of PCT Application) No. 2007-502178 (JP 2007-502178 A) disclose that a dental restoration for implanting is prepared by cutting a dental mill blank with a bolt hole preliminarily formed.

Further, Japanese Unexamined Patent Application Publication (Translation of PCT Application) No. 2004-507316 (JP2004-507316 A) discloses that a dental restoration is prepared by cutting a dental block in a columnar shape, or in a quadratic prism shape.

SUMMARY OF THE INVENTION

In recent years, an increase in speed of cutting of a dental restoration is attempted and thus a cutting method of a dental restoration as quickly as possible is required. However, none of the above described prior art documents discloses the knowledge for shortening a cutting time. In the conventional cutting method of a dental restoration of these prior arts, especially in the case of the conventional dental mill blank in the columnar shape or in the quadratic prism shape as shown in JP2004-507316 A, there is a problem that a time required for cutting, especially for boring increases, and a cutting tool is damaged. Therefore, an increase in speed of cutting of a dental restoration was not sufficiently achieved.

According to one embodiment of the disclosure, provided is a dental restoration producing system of producing a dental restoration from a dental mill blank with one or more through-holes, comprising; a data taking-in section taking in a dental mill blank shape data which indicates a shape of a dental mill blank and includes a position data of one or more through-holes, and a dental restoration shape data which indicates a shape of a dental restoration to be produced, a superposed data generating section generating a superposed data in which the dental restoration is superposed in the dental mill blank based on the dental mill blank shape data and the dental restoration shape data, and a control section controlling cutting of the dental mill blank based on the superposed data, wherein, when the dental restoration includes no through-hole of the dental restoration, the superposed data generating section generates a superposed data in which at least one through-hole among the one or more through-holes of the dental mill blank is not superposed with the dental restoration, when the dental restoration includes a through-hole of the dental restoration, the superposed data generating section generates a superposed data in which at least one through-hole among the one or more through-holes of the dental mill blank is not superposed with the dental restoration and the through-hole of the dental restoration, or a superposed data in which at least one through-hole among the one or more through-holes of the dental mill blank is included in the through-hole of the dental restoration which is larger than the at least one through-hole among the one or more through-holes of the dental mill blank, and the control section controls cutting so that cutting is started from the at least one through-hole among the one or more through-holes of the dental mill blank. According to the dental restoration producing system of the present disclosure, an increase in speed of cutting of a dental restoration is sufficiently achieved.

In the present disclosure, "dental restoration" may include not only a dental restoration having a final form, but also a dental restoration having a form of an intermediate body in the preparation process of the dental restoration.

In the present disclosure, "at least one through-hole among the one or more through-holes of the dental mill blank is not superposed with the dental restoration and the through-hole of the dental restoration" includes the case that at least one through-hole are circumscribed with the dental restoration or the through-hole of the dental restoration.

According to one embodiment of the disclosure, provided is a dental mill blank with one or more through-holes used in the dental restoration producing system according to claim 1, wherein the dental mill blank is in a columnar disk shape formed to have a dimension of 1 to 3 cm (height) by 6 to 15 cm (diameter) and having the through-hole at a position which includes the center of a circular face, or is in a quadratic prism disk shape formed to have a dimension of 1 to 3 cm (height) by 6 to 15 cm (one side) by 6 to 15 cm (one side) and having the through-hole at a position which includes the center of a rectangular face having the dimension of 6 to 15 cm (one side) by 6 to 15 cm (one side). According to the dental mill blank of the present disclosure, an increase in speed of cutting of a dental restoration is sufficiently achieved.

According to one embodiment of the disclosure, provided is a dental mill blank with one or more through-holes used in the dental restoration producing system according to claim 1, wherein the dental mill blank is in a columnar block shape formed to have a dimension of 1 to 2 cm (one side) by 1 to 2 cm (one side) by 1 to 6 cm (height) and having the through-hole at a position spaced from one end of in the longitudinal direction by a distance of 1 to 10% of the dimension in the longitudinal direction, or is in a columnar block shape formed to have a dimension of 1 to 6 cm (height) by 1 to 2 cm (diameter) and having the through-hole at a position spaced from one end of in the height direction by a distance of 1 to 10% of the dimension in the height direction. According to the dental mill blank of the present disclosure, an increase in speed of cutting of a dental restoration is sufficiently achieved.

According to one embodiment of the disclosure, provided is a computer-implemented operation method of a dental restoration producing system for producing a dental restoration from a dental mill blank with one or more through-holes, comprising; a data taking-in step of taking in a dental mill blank shape data which indicates a shape of a dental mill blank and includes a position data of one or more through-holes, and a dental restoration shape data which indicates a shape of a dental restoration to be produced, a superposed data generating step of generating a superposed data in which the dental restoration is superposed in the dental mill blank based on the dental mill blank shape data and the dental restoration shape data, and a cutting step of cutting of the dental mill blank based on the superposed data, wherein, when the dental restoration includes no through-hole of the dental restoration, in the superposed data generating step, a superposed data in which at least one through-hole among the one or more through-holes of the dental mill blank is not superposed with the dental restoration is generated, when the dental restoration includes a through-hole of the dental restoration, in the superposed data generating step, a superposed data in which at least one through-hole among the one or more through-holes of the dental mill blank is not superposed with the dental restoration and the through-hole of the dental restoration, or a superposed data in which at least one through-hole among the one or more through-holes of the dental mill blank is included in the through-hole of the dental restoration which is larger than the at least one through-hole among the one or more through-holes of the dental mill blank, is generated, and the cutting is started from the at least one through-hole among the one or more through-holes of the dental mill blank in the cutting step. According to the computer-implemented operation method of a dental restoration producing system of the present disclosure, increase in speed of the cutting of dental restoration is sufficiently achieved.

According to one embodiment of the disclosure, provided is a non-transitory computer-readable storage medium storing a dental restoration producing program, when executed, causing one or more computers to: a data taking-in section taking in a dental mill blank shape data which indicates a shape of a dental mill blank and includes a position data of one or more through-holes, and a dental restoration shape data which indicates a shape of a dental restoration to be produced, a superposed data generating section generating a superposed data in which the dental restoration is superposed in the dental mill blank based on the dental mill blank shape data and the dental restoration shape data, and a control section controlling cutting of the dental mill blank based on the superposed data, wherein, when the dental restoration includes no through-hole of the dental restoration, the superposed data generating section generates a superposed data in which at least one through-hole among the one or more through-holes of the dental mill blank is not superposed with the dental restoration, when the dental restoration includes a through-hole of the dental restoration, the superposed data generating section generates a superposed data in which at least one through-hole among the one or more through-holes of the dental mill blank is not superposed with the dental restoration and the through-hole of the dental restoration, or a superposed data in which at least one through-hole among the one or more through-holes of the dental mill blank is included in the through-hole of the dental restoration which is larger than the at least one through-hole among the one or more through-holes of the dental mill blank, and the control section controls cutting so that cutting is started from the at least one through-hole among the one or more through-holes of the dental mill blank. According to the non-transitory computer-readable storage medium storing a dental restoration producing program of the present disclosure, increase in speed of the cutting of dental restoration is sufficiently achieved.

DETAILED DESCRIPTION OF THE PREFERRED EMBODIMENTS

Figure 1:
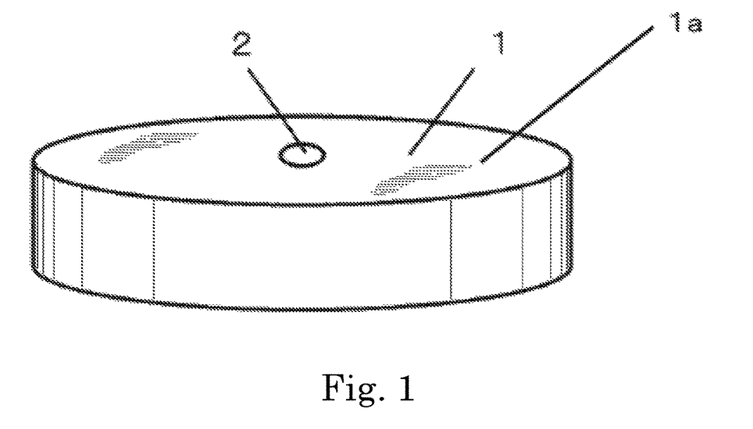
FIG. 1 is a dental mill blank in a columnar disk shape according to one embodiment of the disclosure.

A dental restoration producing system according to one embodiments of the present disclosure and a dental mill blank with one or more through-holes used in the system according to one embodiments of the present disclosure will be described below with reference to the drawings. FIG. 1 shows a dental mill blank 1 in a columnar disk shape as a dental mill blank with one or more through-holes used in the present embodiment. The dental mill blank 1 used in the dental restoration producing system according to present disclosure may have any shape such as one selected from a quadratic prism disk shape, a quadratic prism block shape, a columnar block shape. The dental mill blank 1 in the columnar disk shape shown in FIG. 1 has the dimension of 15 mm (height) by 98 mm (diameter). In the case of a dental mill blank 1 in the columnar disk shape, for example, the dental mill blank 1 may have the dimension of 1.0 to 3.0 cm (height) by 6.0 to 15.0 cm (diameter).

A dental mill blank 1 includes a through-hole 2. In the present embodiment, this through-hole 2 is not included in the final form of a dental restoration to be produced. In other words, the through-hole 2 of present embodiment does not remain on the outer surface of the dental restoration to be produced because all wall surfaces which construct the through-hole 2 are cut during cutting the dental mill blank for preparing the dental restoration. In the present embodiment, the through-hole 2 is formed at the center of an upper circular surface 1a to have a dimension of 3 mm (diameter) and to extend vertically to the upper circular surface 1a. As a result, even if an installation position of the dental mill blank 1 in the radial direction is changed, the through-hole is maintained at the same position. Especially, the through-hole 2 is preferably formed so that the center of the gravity of the through-hole and the center of the gravity of the dental mill blank match with each other.

Figure 2:
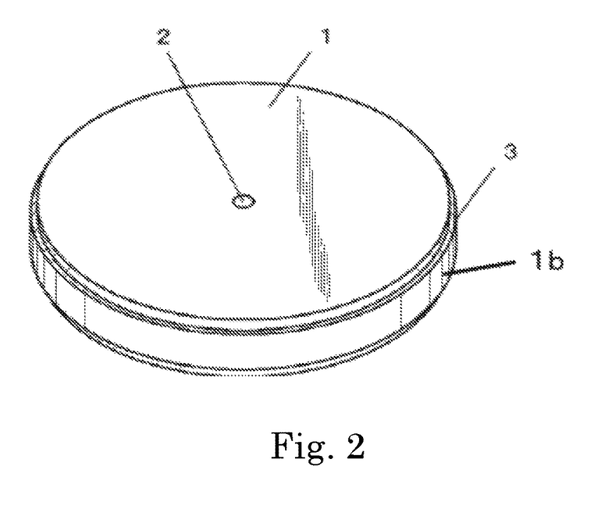
FIG. 2 is a dental mill blank in a columnar disk shape formed with a mounting groove on the circumferential surface according to one embodiment of the disclosure.

FIG. 2 also shows a dental mill blank 1 in a columnar disk shape like FIG. 1. However, a circumferential surface 1b of the dental mill blank of FIG. 2 is formed with a mounting groove 3 for mounting the dental mill blank 1 to a cutting device such as CAD/CAM device (not shown).

In the case of a dental mill blank 1 in a quadratic prism disk shape, for example, the dental mill blank 1 may have the dimension of 1.0 to 3.0 cm (height) by 6.0 to 15.0 cm (one side) by 6.0 to 15.0 cm (one side). In this case, a through-hole is preferably formed near the center of the upper surface have the dimension of 6.0 to 15.0 cm (one side) by 6.0 to 15.0 cm (one side), and the through-hole is preferably formed so that the center of the gravity of the through-hole and the center of the gravity of the dental mill blank match with each other.

Although the through-hole 2 is formed into a columnar shape in FIGS. 1 and 2, for example, the through-hole 2 may be formed into a truncated cone shape. The diameter of the through-hole may be 0.5-20.0 mm, is preferably 1.0-12.0 mm, more preferably 2.0-4.0 mm, because a cutting tool can be easily inserted in the through-hole to perform cutting using the side of the cutting tool. The through-hole 2 may be formed into a triangular prism shape, a quadratic prism shape or a polygonal prism shape.

Figure 3:
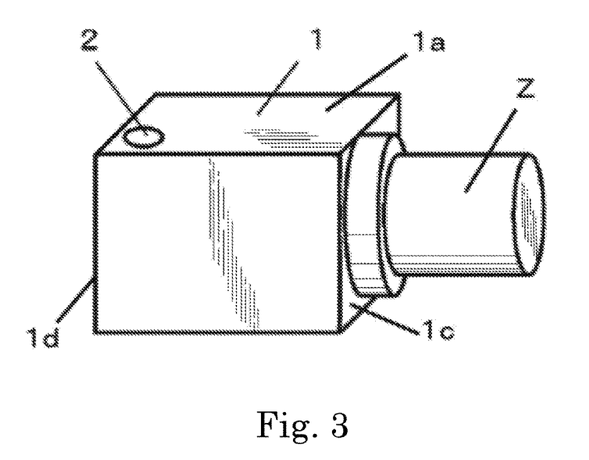
FIG. 3 is a dental mill blank in a quadratic prism block shape according to one embodiment of the disclosure.

FIG. 3 shows a dental mill blank 1 in a quadratic prism block shape. The dental mill blank 1 in a quadratic prism block shape shown in FIG. 3 has, for example, the dimension of 18 mm (longitudinal one side) by 11 mm (one side) by 11 mm (one side). In the case of a dental mill blank 1 in a quadratic prism block shape, for example, the dental mill blank 1 may also have the dimension of 1.0-2.0 cm (one side) by 1.0-2.0 cm (one side) by 1.0-6.0 cm (one side). One of a side surface 1c of the dental mill blank 1 in a quadratic prism block shape shown in FIG. 3 is formed with a jig Z for mounting the dental mill blank 1 to a cutting device. Further, an upper surface 1a of the dental mill blank 1 in FIG. 3 is formed with a through-hole 2. More specifically, the through-hole 2 is formed at a position spaced from a side surface 1d which opposite to the side surface 1c formed with the jig Z, by 1 mm on the upper surface 1a. In the present embodiment, because the through-hole 2 is formed near the side surface 1d opposite to the side surface 1c formed with jig Z, more specifically, is formed at a position spaced from the side surface 1d by a distance of 1 to 10% of the dimension in the longitudinal direction of the dental mill blank 1, cutting may be started from a positon distant from cutting device, therefore, cutting can be carried out easily. It should be noted that in the case of a dental mill blank 1 in a columnar block shape, the dental mill blank 1 may have the dimension of 1.0 to 6.0 cm (height) by 1.0 to 2.0 cm (diameter). In this case, the dimension and the position of a through-hole is the same as the case of a dental mill blank 1 in a quadratic prism block.

Figure 4:
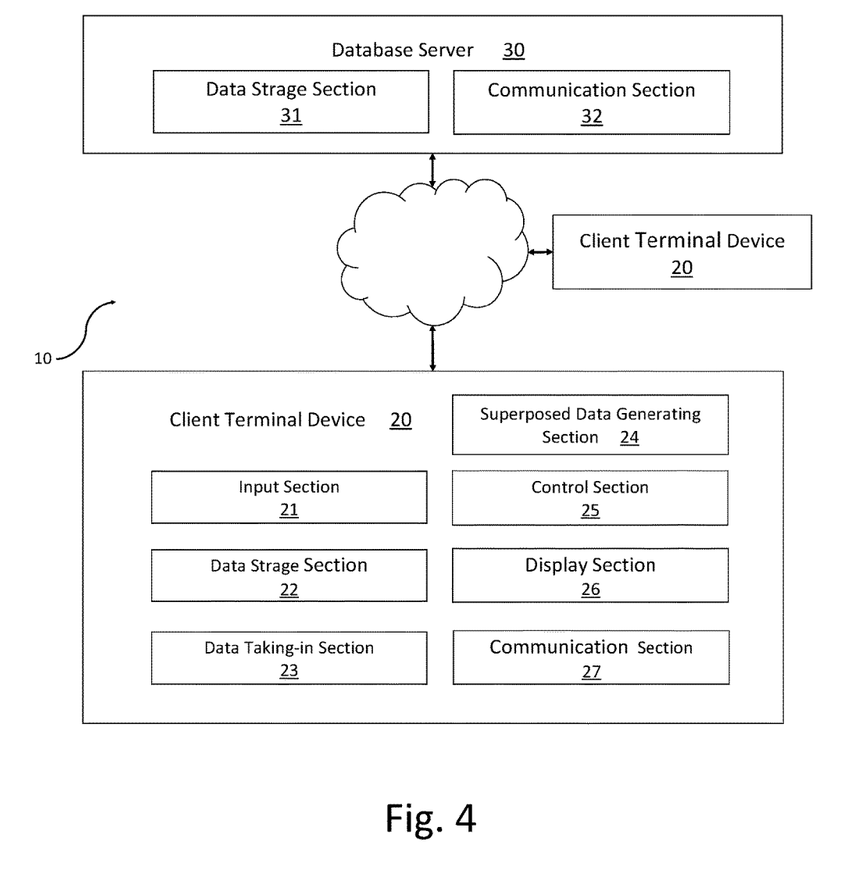
FIG. 4 is a block diagram schematically illustrating a functionality of a dental restoration producing system according to one embodiment of the disclosure.
Figure 5:
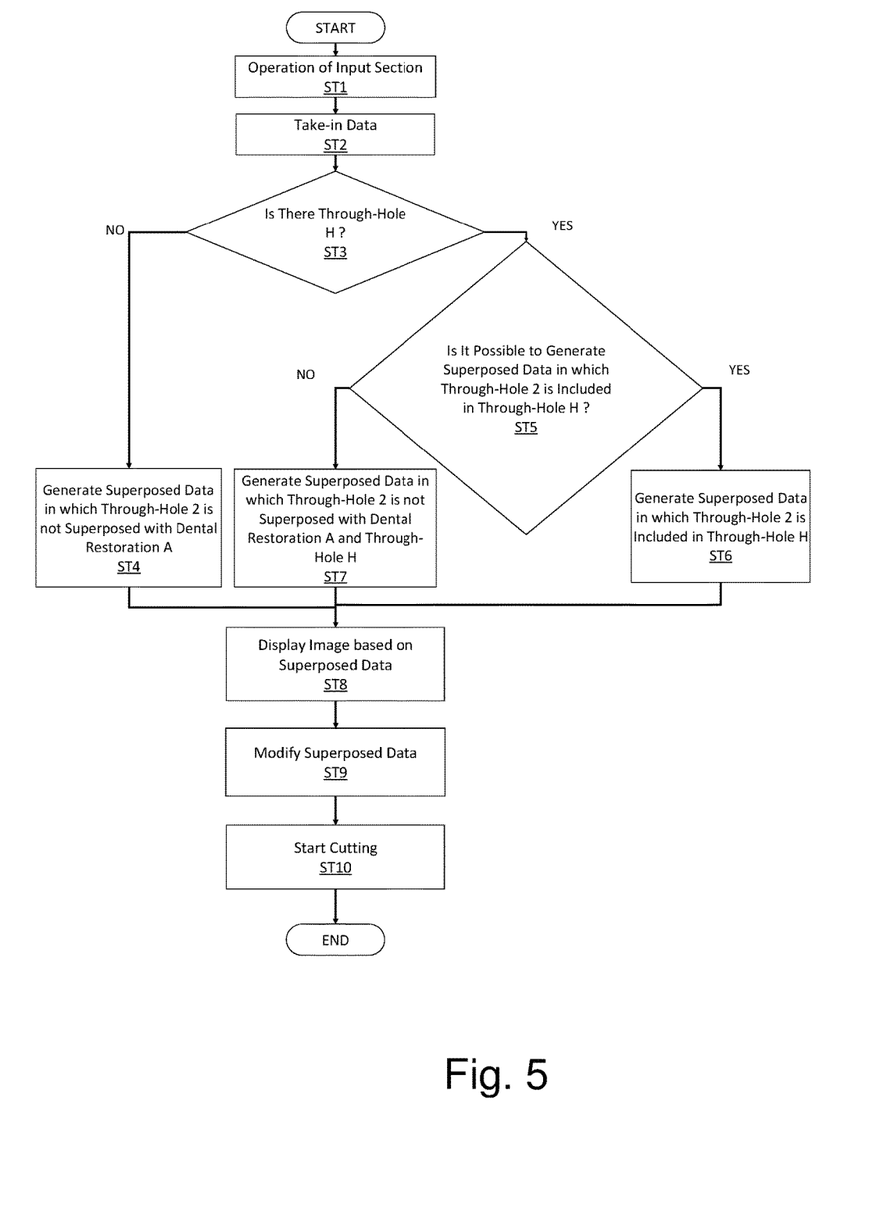
FIG. 5 is one example of flow chart schematically illustrating a process of a dental restoration producing system according to one embodiment of the disclosure.

FIG. 4 shows a block diagram schematically illustrating a functionality of the dental restoration producing system for cutting the dental mill blank 1 having through-hole 2, and FIG. 5 shows an example of a flowchart schematically showing process of the dental restoration producing system for cutting the dental mill blank 1 having through-hole 2.

As shown in FIG. 4, the dental restoration producing system 10 of the present embodiment includes a plurality of client terminal devices 20 and a database server (an external storage device) 30 which are connected to a communication line such as internet line. Firstly, the configurations of the client terminal device 20 and the database server 30 are described.

The client terminal device 20 of the present embodiment is operated by a client such as a dental technician and a dentist, and includes any optional information processing device. The client terminal device 20 of the present embodiment is configured as a personal computer which is a general computer, and includes a central processing unit (CPU/computer processor), a main memory, a user interface (I/F), a communication I/F, and a storage. These components configuring the client terminal device 20 may be electrically connected to one another via a bus. These components configuring the client terminal device 20 may be conventional ones.

The database server 30 of the present embodiment is configured as a usual computer, and includes a central processing unit (CPU/computer processor), a main memory, a user interface (I/F), a communication interface (I/F), a storage, and a disk drive. These components configuring the database server 30 may be electrically connected to one another via a bus. These components configuring the database server 30 may be conventional ones.

Next, a schematic function of the dental restoration producing system 10 shown in FIG. 4 will be described. The client terminal device 20 of the present embodiment includes an input section 21 operated by a client (user) of the client terminal device 20, such as a dental technician and a dentist, a data storage section 22, a data taking-in section 23, a superposed data generating section 24, a control section 25, a display section 26, and a communication section 27. These sections are realized in the client terminal device 20 by cooperatively working each components configuring the client terminal device 20 each other, for example, by executing a program for the dental restoration producing system of the present embodiment.

Further, the database server 30 includes a data storage section 31 and a communication section 32. These sections are realized in the database server 30 by cooperatively working each components configuring the database server 30 each other.

The data storage section 22 stores a dental mill blank shape data which indicates a shape of the dental mill blank 1 and includes a position data of the through-hole 2, and a dental restoration shape data which indicates a shape of a dental restoration to be produced. The data storage section 22 may store a superposed data as described below. These data may be acquired from other client terminal device 20 and/or other database server 30 via the communication section 27. Alternatively, these data may be stored in the data storage section 22 in advance by reading from various storage media.

In the present disclosure, "dental mill blank shape data" is a data which indicates a shape of dental mill blank and includes a position data of a through-hole, and which preferably includes a shape data of the through-hole.

In the present disclosure, "dental restoration shape data" is a data which indicates a shape of a dental restoration to be cut from a dental mill blank. The dental restoration shape data may be prepared, for example, by reading a shape prepared from wax via a 3D-scanner, or by selecting an optional shape from standard shapes to modifying the selected shape according to an individual patient.

The data taking-in section 23 takes in a dental mill blank shape data and a dental restoration shape data based on the input from the input section 21. For example, in one embodiment, the user selects a dental mill blank shape data and a dental restoration shape data, and then the data taking-in section 23 takes-in the selected dental mill blank shape data and the selected dental restoration shape data. In this case, the data taking-in section 23 may take-in the selected dental mill blank shape data and the selected dental restoration shape data from the data storage section 22. Further, in this case, if the selected dental mill blank shape data and/or the selected dental restoration shape data are not stored in the data storage section 22, the data taking-in section 23 may take-in the selected dental mill blank shape data and the selected dental restoration shape data from other client terminal device 20 and/or other database server 30 via the communication section 27. Furthermore, in this case, the selected dental mill blank shape data and the selected dental restoration shape data taken-in via the communication section 27 may be stored in the data storage section 22.

In other embodiment, the user may select only a dental restoration shape data, and then the data taking-in section 23 may take-in the selected dental restoration shape data and extract one or more dental mill blank shape data suitable for preparing a dental restoration to be prepared based on the selected dental restoration shape data. And then the data taking-in section 23 may present the extracted one or more dental mill blank shape data to the user, and may take-in the dental mill blank shape data which is selected by the user among the extracted one or more dental mill blank shape data. In this case, the dental mill blank shape data suitable for preparing a dental restoration to be prepared may be extracted from only the dental mill blank shape data stored in the data storage section 22, or extracted from the dental mill blank shape data stored in the data storage section 22, in the storage section of other client terminal device 20 and/or in the storage section of the database server 30.

The superposed data generating section 24 generates a superposed data in which the dental restoration is superposed in the dental mill blank 1 based on the dental mill blank shape data and the dental restoration shape data which are taken-in by the data taking-in section 23. It is noted that if the dental restoration is superposed with the through-hole 2 of the dental mill blank 1, there is a case in which a dental restoration in desired shape cannot prepared by cutting the dental mill blank. Therefore, with reference to FIGS. 6 and 7, examples of a superposed data generated by the superposed data generating section 24 in case that the dental restoration is superposed in the dental mill blank 1 so that the through-hole 2 is not superposed with the dental restoration, will be described.

Figure 6:
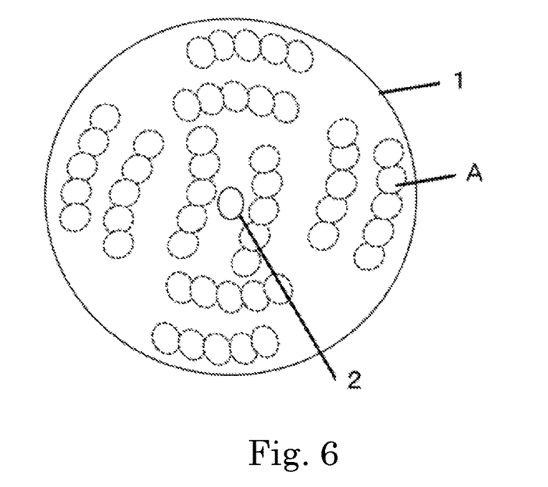
FIG. 6 is one example of a superposed data in case of a dental restoration to be produced with no through-hole.

FIG. 6 shows an example of a superposed data in case that a dental restoration to be produced includes no through-holes. In the example of FIG. 6, the dental restoration A having no through-holes shown by broken lines is superposed in the dental mill blank 1 in a columnar disk shape shown by solid lines. As the example of FIG. 6, when the dental restoration to be produced includes no through-holes of the dental restoration, the superposed data generating section 24 generates a superposed data in which the through-hole 2 of the dental mill blank 1 is not superposed with the dental restoration to be produced.

Figure 7:
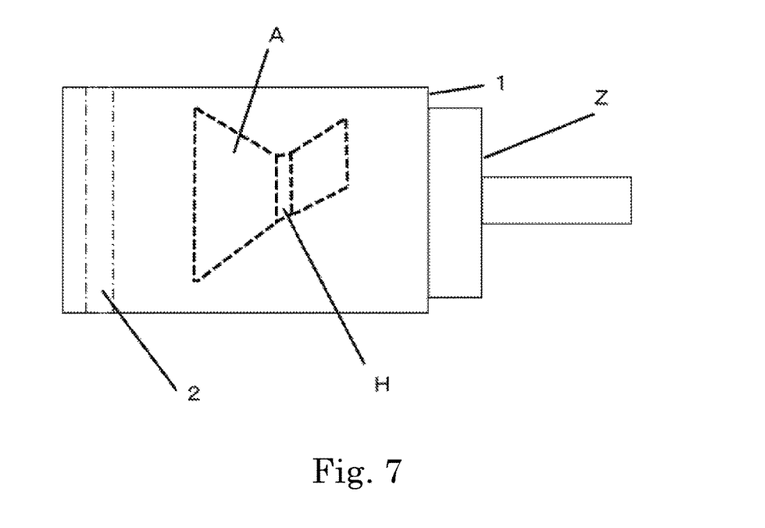
FIG. 7 is one example of a superposed data in case of a dental restoration to be produced with a through-hole.

FIG. 7 shows an example of a superposed data in case that a dental restoration to be produced includes one or more through-holes. In the example of FIG. 7, the dental restoration A having through-hole H shown by broken lines is superposed in the dental mill blank 1 in a quadratic prism block shape shown by solid lines. In the FIG. 7, the position and the shape of the through-hole 2 are shown by dash lines. As the example of FIG. 7, when the dental restoration to be produced includes a through-hole of the dental restoration, the superposed data generating section 24 generates a superposed data in which the through-hole 2 of the dental mill blank 1 is not superposed with the dental restoration to be produced and the through-hole of the dental restoration to be produced.

As shown in FIGS. 6 and 7, a superposed data may be prepared by superposing the shape of the dental restoration to be produced and the shape of the through-hole of the dental restoration to be produced on the dental mill blank 1 so as to avoid superposing on the through-hole 2 of the dental mill blank, and then may be used as a cutting data. It should be noted that although the dental restoration A is disposed so as to form a gap with the through-hole 2 in FIGS. 6 and 7, the dental restoration A may be disposed so as to be partially contact with the through-hole 2. In this case, a part of the wall surface of the through-hole 2 remains on the dental restoration A.

Figure 8:
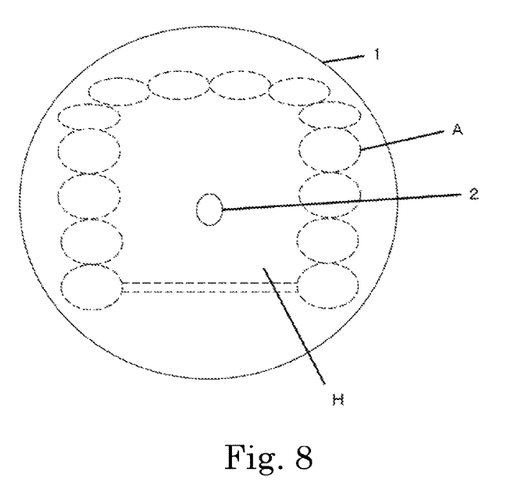
FIG. 8 is another example of a superposed data in case of a dental restoration to be produced with a through-hole.

FIG. 8 shows an example of a superposed data in case that a dental restoration to be produced includes a through-hole H according to other embodiment. In the example of FIG. 8, the dental restoration A including through-hole indicated by broken lines is superposed in the dental mill blank 1 in a columnar disk shape indicated by solid lines. More specifically, in the Example of FIG. 8, the dental restoration A is superposed in the dental mill blank 1 so that the through-hole 2 of the dental mill blank 1 is included in the through-hole H of the dental restoration A, which is larger than the through-hole 2. In this case, the dental restoration A may be disposed so as to be partially contact with the through-hole 2.

In the present embodiment, the superposed data generating section 24 automatically decides a position of the dental restoration to be produced in dental mill blank 1 to generate a superposed data. However, the position of the dental restoration to be produced in dental mill blank 1 may be decided by the operation of the input section 21 by the user of the client terminal device 20 such as a dental technician and a dentist, and the data generating section 24 may generate a superposed data based on the user decision. Further, a position of the dental restoration to be produced, which is decided by the superposed data generating section 24, may be changed based on the operation of the input section 21 by the user of the client terminal device 20 to generate a superposed data. Furthermore, a position of the dental restoration to be produced, which is decided by the operation of the input section 21, may be changed by the superposed data generating section 24 to generate a superposed data.

In the present embodiment, the superposed data generating section 24 outputs the superposed data to a display section 26, and the display section 26 displays an image in which the dental restoration is superposed in the dental mill blank, for example, as shown in FIGS. 6 and 7, to a display screen such as a monitor device. The user of the client terminal device 20 such as a dental technician and a dentist decides whether the position of the dental restoration to be produced in the dental mill blank 1 is appropriate or not based on the image displayed on the display screen, and if need, modifies the superposed data to change the position of the dental restoration to be produced in the dental mill blank 1 to define as cutting data.

In the present embodiment, the superposed data generating section 24 is configured to generate a superposed data in which one of the dental restoration to be produced is positioned near the through-hole 2. More specifically, the superposed data generating section 24 is configured to generate a superposed data in which the distance between the one of the dental restoration to be produced and the through-hole 2 is 0-10 mm, preferably 0.1-5 mm. When the distance is 0 mm, it is possible to start rapidly cutting for producing the dental restoration. When the distance is about 0.1 mm, this distance serves as a margin for cutting. Therefore it is possible to stabilize the motion of a cutting tool when cutting by the cutting tool is started from the through-hole 2. If there is no margin, cutting may be started in a state that an error is generated between the superposed data and the dental mill blank. Therefore, there is a case that a dental restoration in desired shape cannot prepared. When the distance between the one of the dental restoration to be produced and the through-hole 2 is more than 10 mm, the cutting amount from the through-hole 2 for starting the cutting of the dental restoration increase. Therefore, there is a case that increase in speed of the cutting of dental restoration may be not sufficiently achieved.

In the present embodiment, when two or more rental restorations are prepared from one dental mill blank, the data generating section 24 is configured to prepare the superposed data in which the two or more rental restorations are adjacently positioned each other. More specifically, the data generating section 24 is configured to prepare the superposed data in which the distance between the two or more rental restorations adjacently positioned each other is 2-10 mm. When the distance between two adjacent dental restorations is less than 2 mm, cutting of the two adjacent dental restorations may interfere with each other. Therefore, there is a case that a dental restoration in desired shape cannot prepared. When the distance between two adjacent dental restorations is more than 10 mm, the cutting amount for starting the cutting of the adjacent dental restoration increase. Therefore, there is a case that increase in speed of the cutting of dental restoration may be not sufficiently achieved. When the distance between two adjacent dental restorations is more than 3.5 mm, the cutting toll may be used efficiently.

In the present embodiment, when the dental restoration to be prepared is superposed with the through-hole 2 of dental mill blank 1, the superposed data generating section 24 is configured to make the display section 26 display the warning. Therefore, the user of the client terminal device 20 may recognize that it is required to change the position of the dental restoration to be prepared by the displayed warning, to modify the superposed data.

The control section 25 controls cutting of dental mill blank 1 by a cutting tool based on the superposed data which is defined as a cutting data. The control section 25 of the present embodiment controls cutting so that cutting is started from the through-hole 2 of the dental mill blank 1 by the cutting tool. For example, the control section 25 controls cutting of dental mill blank 1 by outputting a control signal of a cutting tool to a CAD/CAM device including the cutting tool.

Next, an example of the specific flow of producing the dental restoration by the dental restoration producing system according to present embodiment will be described in detail with reference to the flowchart of FIG. 5. Firstly, the input section 21 is operated by the user of the client terminal device 20 to select at least a dental restoration shape data (step ST 1). The data taking-in section 23 takes-in the selected dental restoration shape data (and selected dental mill blank shape data) from the data storage section 22, or other client terminal device 20 and/or other data server via the communication section 27 (step ST 2).

The superposed data generating section 24 determines whether the dental restoration of dental restoration shape data taken-in by the data taking-in section 23 includes a through-hole (step ST 3). When the dental restoration to be produced includes no through-holes, the superposed data generating section 24 generates a superposed data in which the dental restoration is superposed in the dental mill blank 1 so that the through-hole 2 of the dental mill blank 1 is not superposed with the dental restoration to be produced (step ST 4). When the dental restoration to be produced includes a through-hole, the superposed data generating section 24 determines whether the dental restoration A is superposed in the dental mill blank 1 so that the through-hole 2 of the dental mill blank 1 is included in the through-hole H of the dental restoration A based on the positon and the dimension of the through-hole 2 and the dimension of the dental mill blank (step ST 5). If the dental restoration A can be superposed in the dental mill blank so that through-hole 2 of the dental mill blank 1 is included in the through-hole H of the dental restoration A, the superposed data generating section 24 generates a superposed data in which dental restoration A is superposed in the dental mill blank 1 so that the through-hole 2 of the dental mill blank 1 is included in the through-hole H of the dental restoration A, which is larger than the through-hole 2 (step ST 6). If the dental restoration A cannot be superposed in the dental mill blank so that through-hole 2 of the dental mill blank 1 is included in the through-hole H of the dental restoration A, the superposed data generating section 24 generates a superposed data in which dental restoration A is superposed in the dental mill blank 1 so that the dental restoration to be prepared and the through-hole H of the dental restoration to be prepared are not superposed with the through-hole 2 of the dental mill blank 1 (step ST 7).

The superposed data generating section 24 outputs the superposed data to the display section 26, and the display section 26 displays an image based on the superposed data to a display screen such as a monitor device (step ST 8). The user of the client terminal device 20, if need, modifies the superposed data to change the position of the dental restoration to be produced in the dental mill blank 1 to define as cutting data. When the dental restoration to be prepared is superposed with the through-hole 2 of dental mill blank 1 in the modified superposed data, the display section 26 displays the warning (step ST 9). The control section 25 controls the cutting tool so that cutting is started from the through-hole 2 of the dental mill blank 1 based on the superposed data which is defined as a cutting data, to cut the dental mill blank 1 (step ST10).

Figure 9:
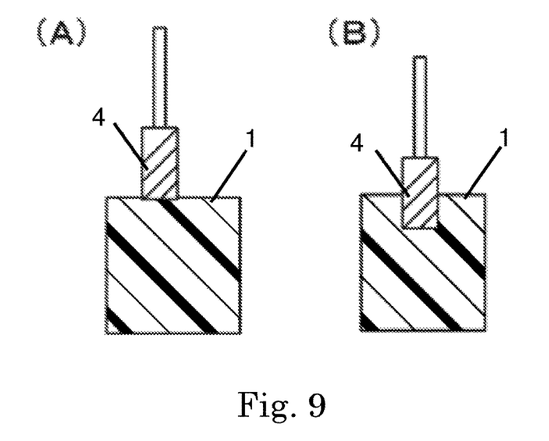
FIG. 9(A) is a schematically view indicating a state just before a start of cutting in prior arts.
FIG. 9(B) is a schematically view indicating a state after a start of cutting in prior arts.

Next, functions and effects provided by the dental restoration producing system according to the present embodiments will be described below with comparing conventional dental restoration producing system. FIG. 9(A) shows a schematically sectional view indicating a state just before a start of cutting in the case of cutting a conventional dental mill blank by conventional dental restoration producing system. FIG. 9(B) shows a schematically sectional view indicating a state after a start of cutting in the case of cutting a conventional dental mill blank by conventional dental restoration producing system. As shown in FIG. 9(A), in the case of cutting a conventional dental mill blank by conventional dental restoration producing system, a tip of a cutting tool 4 in which cutting efficiency is low contacts with the dental mill blank 1 to start cutting so that the dental mill blank 1 is bored by a tip of the cutting tool 4. Therefore, cutting of the dental restoration needs a lot of time. Further, cutting chips with boring can be discharged to only a cutting tool side. Therefore, cutting efficiency decrease. It should be noted that if cutting tool is rotated in order to increase cutting efficiency, there is a case in which a dental restoration in desired shape cannot prepared by cutting the dental mill blank because the size of boring hole increase.

Figure 10:
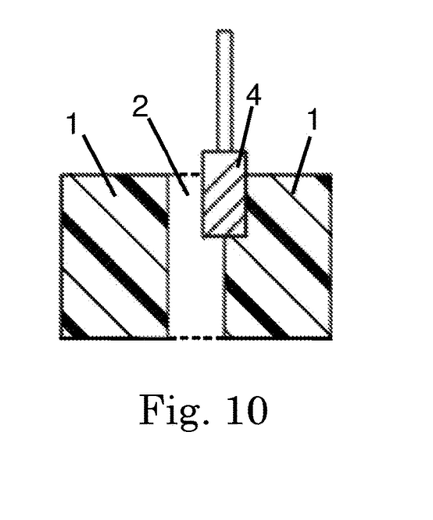
FIG. 10 is a schematically cross sectional view indicating the state that cutting is started from the through-hole.

FIG. 10 shows a schematically cross sectional view of a dental mill blank in case that a dental mill blank of the present embodiment is cut by a dental restoration producing system of the present embodiment. As shown in FIG. 10, in the present embodiment, cutting may be started so that the cutting tool 4 is inserted in the through-hole 2 to cutting the wall surface of the through-hole 2 by the side of the cutting tool 2. Therefore, boring by the tip of the cutting tool 4 is not necessary, and the speed of the cutting of dental restoration increase.

In the above described embodiments, the dental mill blank including one through-hole is explained. However, the dental mill blank according to present disclosure may include two or more through-holes.

The present disclosure may be used in a preparation of a dental restoration by cutting using CAD/CAM system in the dental field.

What is claimed is:

1. A dental restoration producing system of producing a dental restoration from a dental mill blank with one or more through-holes, comprising;
   a data taking-in section taking in a dental mill blank shape data which indicates a shape of a dental mill blank and includes a position data of one or more through-holes, and a dental restoration shape data which indicates a shape of a dental restoration to be produced,
   a superposed data generating section generating a superposed data in which the dental restoration is superposed in the dental mill blank based on the dental mill blank shape data and the dental restoration shape data, and
   a control section controlling cutting of the dental mill blank based on the superposed data, wherein,
   when the dental restoration includes no through-hole of the dental restoration, the superposed data generating section generates a superposed data in which at least one through-hole among the one or more through-holes of the dental mill blank is not superposed with the dental restoration,
   when the dental restoration includes a through-hole of the dental restoration, the superposed data generating section generates a superposed data in which at least one through-hole among the one or more through-holes of the dental mill blank is not superposed with the dental restoration and the through-hole of the dental restoration, or a superposed data in which at least one through-hole among the one or more through-holes of the dental mill blank is included in the through-hole of the dental restoration which is larger than the at least one through-hole among the one or more through-holes of the dental mill blank, and
   the control section controls cutting so that cutting is started from the at least one through-hole among the one or more through-holes of the dental mill blank.

2. A dental mill blank with one or more through-holes used in the dental restoration producing system according to claim 1,
   wherein the dental mill blank is in a columnar disk shape formed to have a dimension of 1 to 3 cm (height) by 6 to 15 cm (diameter) and having the through-hole at a position which includes the center of a circular face, or is in a quadratic prism disk shape formed to have a dimension of 1 to 3 cm (height) by 6 to 15 cm (one side) by 6 to 15 cm (one side) and having the through-hole at a position which includes the center of a rectangular face having the dimension of 6 to 15 cm (one side) by 6 to 15 cm (one side).

3. A dental mill blank with one or more through-holes used in the dental restoration producing system according to claim 1,
   wherein the dental mill blank is in a columnar block shape formed to have a dimension of 1 to 2 cm (one side) by 1 to 2 cm (one side) by 1 to 6 cm (height) and having the through-hole at a position spaced from one end of in the longitudinal direction by a distance of 1 to 10% of the dimension in the longitudinal direction, or is in a columnar block shape formed to have a dimension of 1 to 6 cm (height) by 1 to 2 cm (diameter) and having the through-hole at a position spaced from one end of in the height direction by a distance of 1 to 10% of the dimension in the height direction.

4. A computer-implemented operation method of a dental restoration producing system for producing a dental restoration from a dental mill blank with one or more through-holes, comprising;
   a data taking-in step of taking in a dental mill blank shape data which indicates a shape of a dental mill blank and includes a position data of one or more through-holes, and a dental restoration shape data which indicates a shape of a dental restoration to be produced,
   a superposed data generating step of generating a superposed data in which the dental restoration is superposed in the dental mill blank based on the dental mill blank shape data and the dental restoration shape data, and
   a cutting step of cutting of the dental mill blank based on the superposed data, wherein,
   when the dental restoration includes no through-hole of the dental restoration, in the superposed data generating step, a superposed data in which at least one through-hole among the one or more through-holes of the dental mill blank is not superposed with the dental restoration is generated,
   when the dental restoration includes a through-hole of the dental restoration, in the superposed data generating step, a superposed data in which at least one through-hole among the one or more through-holes of the dental mill blank is not superposed with the dental restoration and the through-hole of the dental restoration, or a superposed data in which at least one through-hole among the one or more through-holes of the dental mill blank is included in the through-hole of the dental restoration which is larger than the at least one through-hole among the one or more through-holes of the dental mill blank, is generated, and
   the cutting is started from the at least one through-hole among the one or more through-holes of the dental mill blank in the cutting step.

5. A non-transitory computer-readable storage medium storing a dental restoration producing program, when executed, causing one or more computers to:
   a data taking-in section taking in a dental mill blank shape data which indicates a shape of a dental mill blank and includes a position data of one or more through-holes, and a dental restoration shape data which indicates a shape of a dental restoration to be produced,
   a superposed data generating section generating a superposed data in which the dental restoration is superposed in the dental mill blank based on the dental mill blank shape data and the dental restoration shape data, and
   a control section controlling cutting of the dental mill blank based on the superposed data, wherein,
   when the dental restoration includes no through-hole of the dental restoration, the superposed data generating section generates a superposed data in which at least one through-hole among the one or more through-holes of the dental mill blank is not superposed with the dental restoration,
   when the dental restoration includes a through-hole of the dental restoration, the superposed data generating section generates a superposed data in which at least one through-hole among the one or more through-holes of the dental mill blank is not superposed with the dental restoration and the through-hole of the dental restoration, or a superposed data in which at least one through-hole among the one or more through-holes of the dental mill blank is included in the through-hole of the dental restoration which is larger than the at least one through-hole among the one or more through-holes of the dental mill blank, and the control section controls cutting so that cutting is started from the at least one through-hole among the one or more through-holes of the dental mill blank.

* * * * *